United States Patent
Breidenthal et al.

[11] Patent Number: 5,888,193
[45] Date of Patent: Mar. 30, 1999

[54] ENDOSCOPE WITH CURVED OPTICAL AXIS

[75] Inventors: Robert S. Breidenthal, Bolton; Richard E. Forkey, Westminster; Jack Smith, Sudhury; Brian E. Volk, Jefferson, all of Mass.

[73] Assignee: Precision Optics Corporation, Gardner, Mass.

[21] Appl. No.: 966,826

[22] Filed: Nov. 10, 1997

Related U.S. Application Data

[63] Continuation-in-part of Ser. No. 883,216, Jun. 26, 1997, which is a continuation-in-part of Ser. No. 605,593, Feb. 22, 1996, abandoned.

[51] Int. Cl.[6] .................................................. A61B 1/002
[52] U.S. Cl. ........................ 600/160; 359/435; 600/130; 600/138
[58] Field of Search .................................... 600/138, 139, 600/130, 141, 142, 160, 167, 174; 359/434, 435

[56] References Cited

U.S. PATENT DOCUMENTS

| | | |
|---|---|---|
| 878,917 | 2/1908 | Wappler . |
| 1,915,811 | 6/1933 | Wolf ......................................... 600/139 |
| 2,507,935 | 5/1950 | Richmond . |
| 3,297,022 | 9/1963 | Wallace . |
| 3,326,620 | 6/1967 | Marie ....................................... 359/435 |
| 3,382,022 | 5/1968 | Fox .......................................... 359/435 |
| 3,414,344 | 12/1968 | Mukojima ................................ 359/435 |
| 3,506,331 | 4/1970 | Kompfner ................................ 359/435 |
| 4,148,551 | 4/1979 | Macanally ................................ 359/435 |
| 5,184,602 | 2/1993 | Anapliotis et al. . |
| 5,210,814 | 5/1993 | McNally . |
| 5,309,541 | 5/1994 | Flint ......................................... 359/435 |
| 5,323,767 | 6/1994 | Lafferty . |
| 5,512,034 | 4/1996 | Finn et al. . |

*Primary Examiner*—John P. Leubecker
*Attorney, Agent, or Firm*—Pearson & Pearson

[57] ABSTRACT

An endoscope has an elongated sheath that follows a curved path. The sheath houses a plurality of relay lens sets designed to have a maximum usable field of view that is greater than the size of an image to be produced. Discrete lens elements within the image transfer guide allow the image to offset to the edges of the maximum usable field of view thereby to allow the axes through the individual sets to progressively shift in angle to form the curved path. This provides endoscopes that are particularly useful as arthroscopes or

7 Claims, 4 Drawing Sheets

ENDOSCOPE WITH CURVED OPTICAL AXIS

CROSS-REFERENCE TO RELATED APPLICATION

This application is a continuation-in-part of co-pending patent application Ser. No. 08/883,216 filed Jun. 26, 1997 titled Endoscope with Low Distortion and assigned to the same assignee as this invention, which is a continuation-in-part of U.S. patent application Ser. No. 08/605,593 filed Feb. 22, 1996 (now abandoned).

BACKGROUND OF THE INVENTION

1. Field of the Invention

This invention generally relates to optical systems and more specifically to endoscopes having an image transfer guide that lies along a curved optical axis.

2. Description of Related Art

Endoscopes have attained great acceptance within the medical community in connection with a number of procedures primarily because they provide a means for performing procedures with minimal patient trauma by enabling a physician to view directly the internal anatomy of a patient. Over the years a number of endoscopes have been developed and have been categorized according to specific applications. Many have specific names including arthroscopes, cystoscopes, proctoscopes, laparoscopes. Industrial endoscopes are often called borescopes.

In whatever form, an endoscope generally comprises an objective lens system at the distal end of the endoscope that forms an image of an object. With medical endoscopes, the object is generally within a patient in some environmental media such as air, water, a saline solution or the like. With industrial endoscopes the object may be located in a remote enclosed volume. An eyepiece or ocular system at the proximal end presents the image for viewing visually, electronically or otherwise externally of the patient or enclosed volume. An image transfer system intermediate the objective and the eyepiece systems transfers the image produced by the objective lens system to the eyepiece system.

Endoscopes are classified by different applications that impose various optical and physical requirements including size of the field of view, image quality, maximum acceptable outer diameters, length and whether the endoscope should be rigid or flexible. Two particular applications for endoscopes to which this invention is particularly adapted are arthroscopes and laryngoscope. Arthroscopic procedures require a relatively thin probe that is inserted into a joint to be examined. The resulting image must have good spatial and contrast resolution to allow a physician to diagnose any injury in the joint being examined, such as the knee, and to undertake appropriate treatment. Typical endoscopes are either forward or downward looking. While forward or obliquely viewing endoscopes can often have a fairly significant field of view, complete diagnosis for damage in the knee joint often requires a wider view than even conventional endoscopes can provide. Different approaches have been taken to improve the imaging of knee joints including the use of a periscope like structure as disclosed in U.S. Letters Pat. No. 5,188,093 to Lafferty et al. In that endoscope a cylindrically shaped rod of a material having a cylindrical gradient refractive index attaches to the distal end of a scope needle that is slidably introduced through the cannula of a catheter or auxiliary lumen of an endoscope. Light reflected from the interior structure of a joint enters the distal base of this rod and is focused onto its proximal base. The image guide is bent near its distal portion to form an angle of about 25° between the distal portion of the image guide and the axis of the probe, so the axis of the rod is not parallel to the probe axis. A fiber optic image guide transfers the image from the distal end of the arthroscope to the proximal end.

U.S. Letters Pat. No. 5,512,034 discloses another version of an endoscopic device with a bent distal tip portion that carries an objective lens. This approach also utilizes a fiber optic image guide to transfer the image formed by the objective lens system to the proximal end of the structure.

As is known, spatial and contrast resolution from fiber optic image guides is inferior to the corresponding image characteristics provided by a properly designed relay lens system. However, typical relay lens systems are rigid structures that lie along a straight optical axis. Viewing off this central axis is accomplished by designing an objective lens that views along a field of view axis that diverges distally from the central endoscope axis. However, these structures limit the amount by which the field of view axis can diverge from the central endoscope axis. It has been found that many arthroscope procedures could benefit from a greater angle of divergence than possible with conventional relay systems, relay systems being preferred because of their improved optical characteristics.

For similar reasons laryngoscopes are also typically rigid straight endoscopes that comprise relay lens systems so that the image viewed in the larynx is of high quality. It would be helpful if a laryngoscope could be curved to more closely match the curved passage from the mount to the larynx.

SUMMARY

Therefore it is an object of this invention to provide an endoscope with a relay lens image transfer guide that follows a curved path.

Another object of this invention is to provide an improved endoscope with relay lens sets for transferring an image from the distal end to the proximal end along a curved path.

Still another object of this invention is to provide an arthroscope with a curved image guide of discrete lens elements that improves the area that can be viewed from a given proximal position of the arthroscope.

Yet another object of this invention is to provide a laryngoscope which utilizes a relay lens image guide in a sheath that is curved to match more closely the passage from the mouth to the larynx.

In accordance with this invention an endoscope includes a sheath extending between proximal and distal ends. The sheath has a curved portion whereby a central axis at the distal end of the sheath diverges from a central axis at the proximal end of the curved portion. An objective lens at the distal end forms an image within a field of view of the objective lens. A plurality of discrete lens elements disposed along the interior of the sheath direct light received from the objective lens along the distal end central axis to the proximal end central axis. The discrete lens elements are organized into relay lens sets. The central axes at each end of a relay lens set diverge.

BRIEF DESCRIPTION OF THE DRAWINGS

The appended claims particularly point out and distinctly claim the subject matter of this invention. The various objects, advantages and novel features of this invention will be more fully apparent from a reading of the following detailed description in conjunction with the accompanying drawings in which like reference numerals refer to like parts, and in which:

DESCRIPTION OF ILLUSTRATIVE EMBODIMENTS

Figure 1:
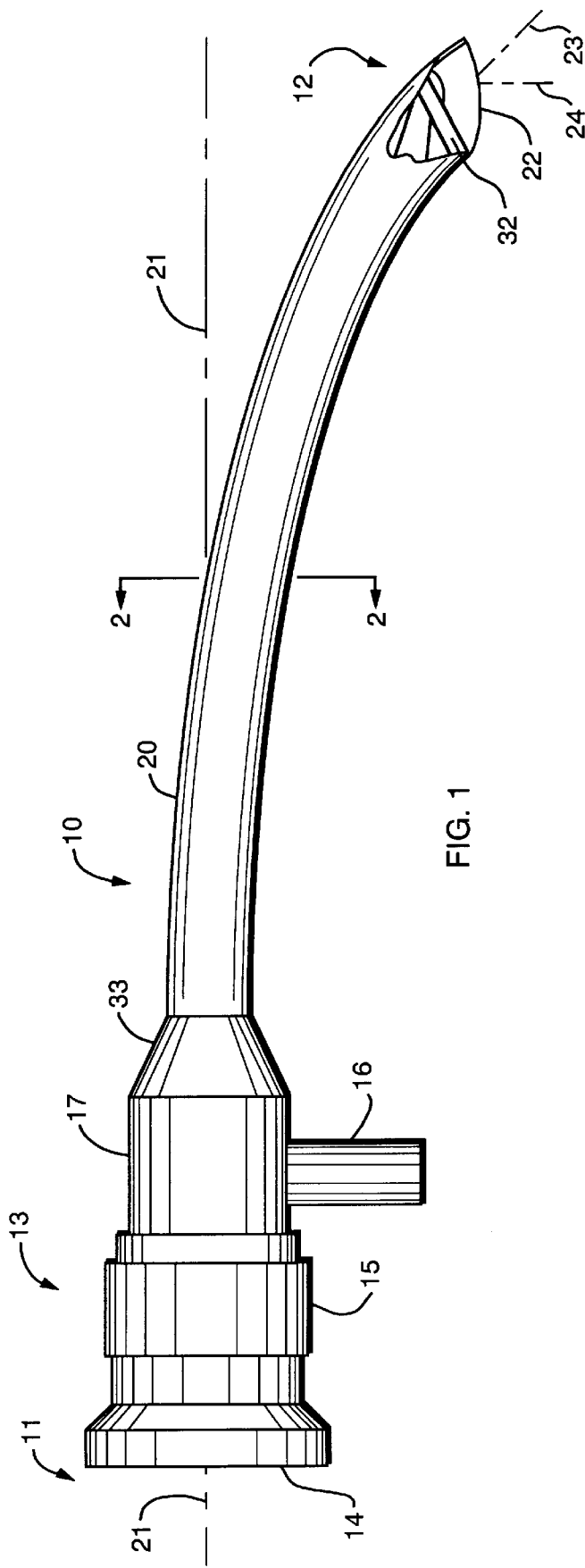
FIG. 1 is a view of an endoscope constructed in accordance with this invention.

FIG. 1 depicts an endoscope 10. such as an arthroscope or laryngoscope, that extends between a proximal end 11 and a distal end 12. At the proximal end 11 an eyepiece 13 provides a means for viewing an object at the distal end 12. The eyepiece may be adapted for direct viewing or viewing through a remote display such as a television display connected at an eye shield or coupler 14. The eyepiece may include a focus ring 15. A light source adapter 16 typically receives a fiber optic bundle from a light source (not shown but known in the art) for directing light to the distal end 12. A housing 17 at the eyepiece 13 provides a volume for containing the light pipe and lens elements that form the eyepiece 13.

The endoscope 10 in FIG. 1 also contains a sheath 20 that extends distally from the eyepiece 13. As will be apparent, the proximal end of the sheath 20 lies on a central endoscope axis 21 that constitutes a central axis at the proximal end. The sheath 20 follows a curved path to the distal end 12 to point in a direction along a central axis 23 at the distal end 12. As will be apparent the axes 21 and 23 are divergent. As shown in FIG. 1 the endoscope 10 is also characterized by a field of view axis 24 which is a central axis through the field of view established by an objective lens. As will become apparent, the image transfer guide contained in the sheath 20 of endoscope 10 "bends" the optical path between the distal end 12 and the proximal end at the eyepiece 13.

Figure 2:
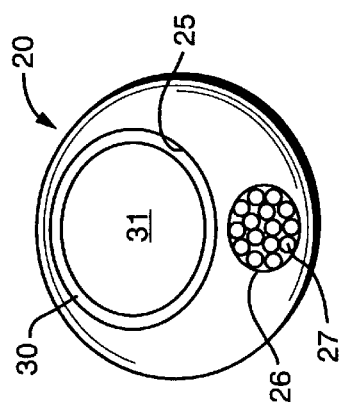
FIG. 2 is a cross-section along lines 2—2 in FIG. 1.

FIG. 2 is a cross-section of the sheath 20 and the components it contains. More specifically the sheath 20 has formed therethrough a circular lens lumen 25 and a light path lumen 26 that can have a circular shape or any other shape that will optimize the cross-section of an optical fiber 27 carried in the lumen 26 to produce a required intensity at the distal and for illuminating an object.

The lens lumen 25 typically carries a thin internal housing 30 that constitutes a sheath of a sub assembly that forms the image guide and the objective lens. FIG. 2 depicts the image guide, that comprises a plurality of discrete lens elements, by referencing one element 31 visible from the section line 2—2.

Referring back to FIG. 1 the endoscope 10 includes an objective lens assembly 32 at the distal end that produces an image at its proximal end corresponding to any object within the field of view defined by the field of view axis 24. An objective lens system such as disclosed in co-pending application Ser. No. 08/883,216 provides an image of good quality. At its proximal end the light carrying the image is directed parallel to the central distal end axis 23.

Figure 3:
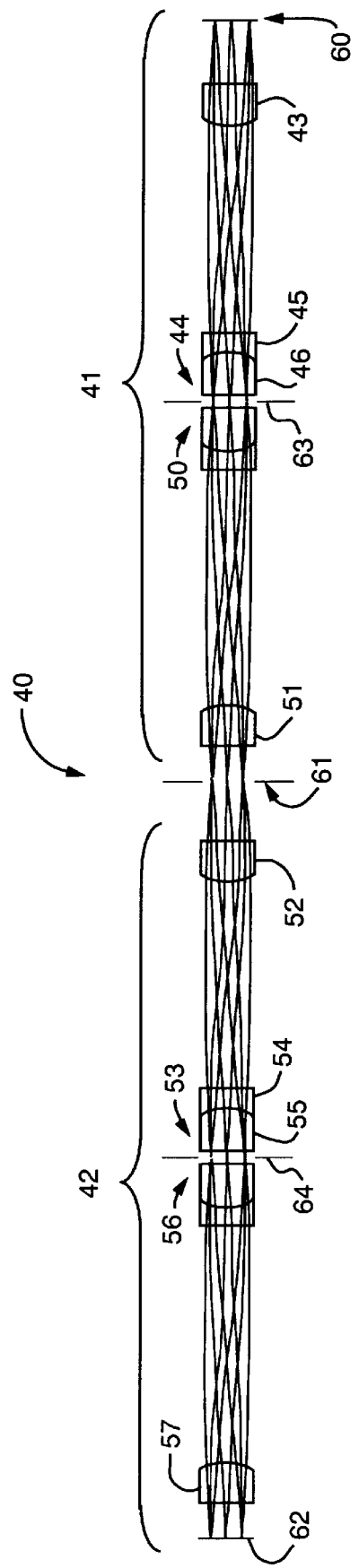
FIG. 3 is a layout of discrete lens elements in two relay lens sets.

Before describing the structure of the relay lens sets that form the image transfer guide of this invention, it will be helpful to specify certain properties of relay lens sets that are useful in understanding this invention. FIG. 3 depicts two sections of a relay lens system 40 including a distal relay lens set 41 and proximal relay lens set 42. These relay lens sets can also be constructed as specified in copending U.S. application Ser. No. 08/883,216. FIG. 3 does not depict an outer sheath, such as the sheath 30 for purposes of clarity.

In this embodiment the relay lens set 41 includes, from the distal to proximal ends, a plano convex lens 43, a doublet 44 including a concave convex lens 45 and a biconvex lens 46. A doublet 50 has the same construction as the doublet 44 but is reversed 180°. A plano convex lens 51 is the last or proximal lens in the lens set 41. The proximal lens set 42 comprises a plano convex lens 52, a doublet 53 including lenses 54 and 55, a doublet 56 and a plano convex lens. 57 having corresponding constructions to the elements in the relay set 41.

The image guide then reforms an image at location 60 as an image at location 61. The relay lens set 42 reforms the image 61 at a proximal image position 62. The relay lens set typically will also include an aperture stop 63 in the relay lens set 41 and an aperture stop 64 in the relay lens set 42 between corresponding doublet lenses.

Still referring to FIG. 3, a series of traces from the ends of the images 60, 61 and 62 at edges and center are disclosed. These ray traces, for a conventional relay set along a straight axis or optical path, define a maximum field of view that corresponds to the maximum size of the image to be transferred. The field of view size depends upon various characteristics of the discrete lens elements. Generally the field of view corresponds to a maximum usable field of view that in turn corresponds to an area over the discrete lens element or set of discrete lens elements through which an image can pass without distorting or otherwise degrading the quality of the image beyond limits imposed by a particular application.

When lens symmetry is used in the construction of a relay, certain aberrations introduced by the individual's relays cancel. These include lateral color, distortion and coma. Other aberrations, such as astigmatism, spherical aberrations and field of curvature, are additive. However, when multiple relay sets are used, the additive aberrations tend to limit the size of the maximum usable field of view. In any event, the image in the relay lens system 40 of FIG. 3 can have a size that corresponds to the maximum usable size of the field of view. Moreover for maximum brightness the aperture stops such as aperture stops 63 and 64 will also correspond to the maximum usable f-number.

Figure 4:
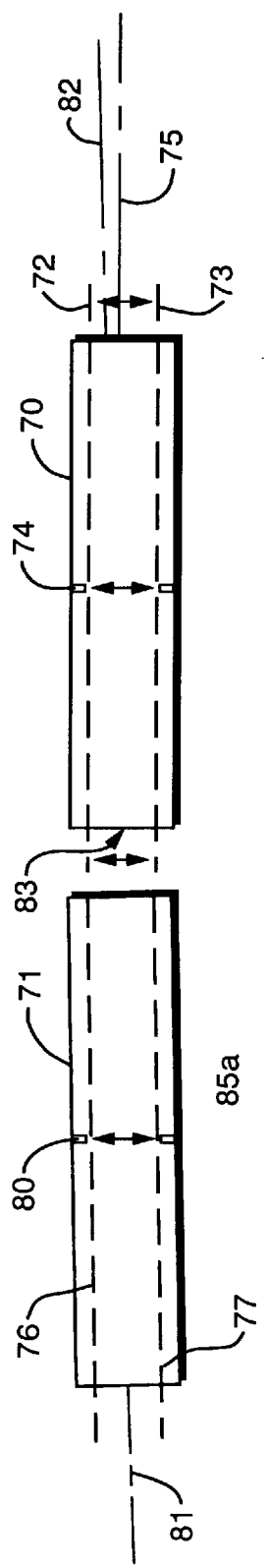
FIG. 4 is a diagram in schematic form of two relay lens sets configured in accordance with this invention.

To assist in an understanding of the process by which the relay lens sets bend the light rays in accordance with this invention, FIG. 4 depicts two relay lens sets 70 and 71 in block form. Each set has a central aperture stop and a maximum usable field of view. More specifically, the relay set 70 has a maximum usable field of view at focus 60 depicted by dashed lines 72 and 73. In addition an axis 75 that is centrally located with respect to the relay lens set 70 extends from the distal end as a distal end central axis 75.

Likewise the relay set 71 is characterized by a maximum usable field of view at 62 shown by dashed lines 76 and 77. An axis extends from the proximal end of the relay set 71 as a central proximal end axis 81.

Further in accordance with this invention, the image at an intermediate focus 61 has a size that is less than the maximum usable field of view size. In this particular embodiment the relay lens set 70 is tilted downward at the distal end such that its central distal axis 75 diverges from an extension 82 of the central proximal end axis 81. Typically the relay lens set 70 will be rotated, clockwise in this specific example, about a pivot point at a center point 83 at the proximal end of the relay lens set 70. The limit of rotation is determined when the image reaches the edge of the maximum usable field of view. In FIG. 4 a light bundle is centered in the aperture stop 80. The relay set 70 tilts until the light bundle shifts to the dashed line 72 representing the upper limit on the maximum usable aperture. Thus, when each of the relay lens sets 70 and 71 are considered as having internal central axes that define straight optical paths, the individual relay sets 70 and 71 can be rotated relative to each other thereby to have a central distal end axis 75 that is diverging from the central proximal axis 81.

As previously indicated the size of the maximum usable field of view depends upon a number of considerations including the particular application. In some diagnoses image vignetting may be acceptable for a decrease in the radius of curvature.

Figure 5:
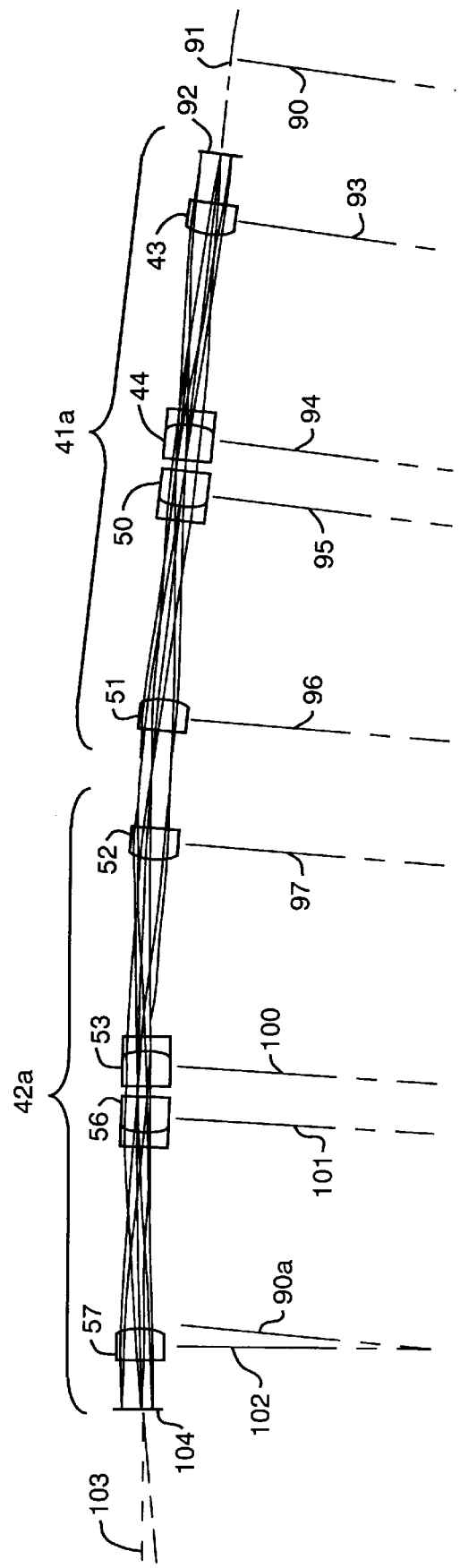
FIG. 5 is a lens diagram of two relay sets configured in accordance with a preferred embodiment of this invention.

FIG. 5 depicts a preferred embodiment of this invention using the same discrete lens elements as shown in FIG. 3 but individually positioned along a curved path. In this articular embodiment a center line 90 represents a plane that is transverse to the figure and normal to a central distal end axis 91 along which an image 92 is formed. The plano convex lens 43 lies in a transverse plane 93 that is slightly oblique with respect to the plane 90. In this particular figure the image is shown as being at the maximum usable field of view at the upper portion of the discrete lens element 43. The lens element 43 redirects the light to the doublets 44 and 50 that individually lie in planes 94 and 95 that are oblique to each other and to the plane 93 with all the planes having a common intersection point that constitutes a center of curvature. The image from the doublet 50 transfers to the plano convex lens 57 on a transverse plane 96 that is angularly displaced with respect to the others. The image exits the lens 57 with the image being at the upper limit position as defined by the maximum usable field of view.

The relay set 42a includes the plano convex lens 52 in plane 97, the doublets 53 and 56 oriented with respect to planes 100 and 101 and the proximal plano convex discrete lens element 57 on the plane 102. Each plane shifts angularly counterclockwise as previously described.

In FIG. 5, the relative angular positions of the planes 90 and 102 are more clearly seen by transferring a center line 90c that is parallel to the plane designated by the center line 90 to the center line 102. From this it can be seen that the image is now being transferred along a central proximal axis that is diverging from the axis. Moreover all the planes 90 through 97 and 100 through 102 converge at a common center of curvature so the lens centers can be defined as having a constant radius of curvature.

In a specific embodiment using the lens layout of FIG. 5 designed according to the specific parameters in Ser. No. 08/833,216, the distance between the images 92 formed at the distal end of FIG. 5 and the image 104 formed at the proximal end was divided into a number of equal arcuate segments such that certain segments terminated at individual lens elements. In this embodiment there were twenty segments. The desired bend was 8°, so each segment was to provide a 0.40 bend or displacement. Each of the planes 90 through 97 and 101 through 102 was shifted by an amount corresponding to the cumulative angular displacement. That is, the approximate angular displacements are 0.4°, 1.8°, 2.2°, 3.6°, 4.4°, 5.6°, 6°, 7.6° for the lens elements 43, 44, 50, 51, 52, 53, 56 and 57, respectively. This provides angular shift between the axes 91 and 103 of 8° and a radius of curvature of about 560 mm.

It has also been found that over a pair of relay sets an image that is centered at the image plane at the entrance of a relay, such as image plane 104, is laterally offset at the next image plane, such as shown at the image between the singlets 51 and 52. However, a next relay set in the proximal direction being a mirrored arrangement of the lens set that caused the offset would be characterized by having the image recentered at the image plane exiting the relay 42a at the plane 92. Stated differently, if an image is being conveyed from left to right in FIG. 5, the image, being laterally offset between the singlets 51 and 52, recenters between the singlet 43. Thus in a preferred embodiment the curved portion of the image guide will contain pairs of relay sets to facilitate the placement and design of the optics associated with the eyepiece.

It is also a desirable design feature that the relay lens sets be telecentric. If they are not, unnecessary vignetting can occur and vignette the image with only minimal bending. In summary there has been disclosed an endoscope that is characterized by an image transfer guide composed of discrete lens elements arranged in a plurality of relay sets. A particular relay set has been disclosed but it will be apparent that any other configuration could be substituted with the achievement of all or some of the above enumerated objects and advantages. Providing the ability to curve the optical path therefore allows the sheath containing the image transfer guide to follow a curved path or be bent. When the endoscope is used for arthroscopic procedures this can result in an ability for the physician to view greater portions of a joint under investigation because, as particularly shown in FIG. 1, a field of view axis from the objective lens can actually achieve an angle of 0° to greater than 90° to provide a possible "backward" look in the joint. In terms of diagnosis of the larynx, the laryngoscope can have a curved path that better matches the throat passage to the larynx. Moreover, in accordance with this invention the use of relay lens sets of the type disclosed provides spatial and contrast resolution in the images that are superior to those that fiber optic systems produce.

This invention has been disclosed in terms of certain embodiments. It will be apparent that many modifications can be made to the disclosed apparatus without departing from the invention. Therefore, it is the intent of the appended claims to cover all such variations and modifications as come within the true spirit and scope of this invention.

What is claimed as new and desired to be secured by Letters Patent of the United States is:

1. An endoscope comprising for viewing an object:
   A) a sheath extending between proximal and distal ends and having a curved portion therein whereby a central axis at the distal end diverges from a central axis at the proximal end of the curved portion,
   B) objective lens means at the distal end of said sheath for forming an image of the object within the field of view of said objective lens, and
   C) a plurality of relay lens sets being disposed along the interior of said sheath for directing light received from said objective lens means along the distal end central axis to the proximal end central axis, at least one of said relay lens sets including plurality of spaced, discrete lens elements at proximal and distal ends of said each relay lens set, said lens elements being positioned such that a proximal end central axis and a distal end central axis diverge.

2. An endoscape as recited in claim 1 wherein said plurality of lens elements in each said relay lens set is formed in a symmetrical pattern.

3. An endoscope as recited in claim 2 wherein at least one of said relay lens sets is characterized by a usable field of view that is greater in size than the image from said objective lens.

4. An endoscope as recited in claim 3 wherein at least one of said relay lens sets comprises a central aperture stop, a pair of oppositely facing doublet lenses equally spaced from said aperture stop and a pair of oppositely facing single lenses equally spaced from said doublet lens.

5. An endoscope as recited in claim 1 wherein each of said discrete lens elements in a relay lens set lies in a plane and successive planes converging at a center of curvature.

6. An endoscope as recited in claim 5 wherein said curved portion comprises n relay lens sets wherein n is an even number.

7. An endoscope as recited in claim 6 wherein each of a said relay lens sets comprises a central aperture stop, a pair of oppositely facing doublet lens equally spaced from said aperture stop and a pair of oppositely facing single lens equally spaced from said doublet lens.

* * * * *